US009028866B2

(12) United States Patent
Pfirrmann et al.

(10) Patent No.: US 9,028,866 B2
(45) Date of Patent: May 12, 2015

(54) METHODS AND COMPOSITIONS FOR ORAL PHARMACEUTICAL THERAPY (75) Inventors: Rolf W. Pfirrmann, Weggis (CH); Peter Geistlich, Stansstad (CH)

(73) Assignee: Geistlich Pharma AG, Wolhusen (CH)

( * ) Notice: Subject to any disclaimer, the term of this patent is extended or adjusted under 35 U.S.C. 154(b) by 126 days.

(21) Appl. No.: 13/701,372

(22) PCT Filed: Jun. 1, 2011

(86) PCT No.: PCT/IB2011/001539
§ 371 (c)(1),
(2), (4) Date: Nov. 30, 2012

(87) PCT Pub. No.: WO2011/151722
PCT Pub. Date: Dec. 8, 2011

(65) Prior Publication Data
US 2013/0089606 A1    Apr. 11, 2013

Related U.S. Application Data (60) Provisional application No. 61/350,183, filed on Jun. 1, 2010, provisional application No. 61/370,315, filed on Aug. 3, 2010.

(51) Int. Cl.
| | | |
|---|---|---|
| A61K 31/549 | (2006.01) | |
| A61K 9/28 | (2006.01) | |
| A61K 9/48 | (2006.01) | |
| A61K 31/54 | (2006.01) | |
| A61K 31/541 | (2006.01) | |

(52) U.S. Cl.
CPC ............. *A61K 31/549* (2013.01); *A61K 9/2846* (2013.01); *A61K 9/485* (2013.01); *A61K 9/4891* (2013.01); *A61K 31/54* (2013.01); *A61K 31/541* (2013.01); *A61K 9/4825* (2013.01)

(58) Field of Classification Search
CPC .......................... A61K 9/4891; A61K 31/549
See application file for complete search history.

(56) References Cited

U.S. PATENT DOCUMENTS

| 5,637,320 A * | 6/1997 | Bourke et al. ................. 424/489 |
| 5,972,933 A * | 10/1999 | Pfirrmann .................. 514/222.5 |
| 6,251,896 B1 | 6/2001 | Costin |
| 6,521,616 B2 * | 2/2003 | Calabresi et al. .......... 514/222.5 |
| 6,555,534 B1 | 4/2003 | Costin |
| 2004/0170617 A1 | 9/2004 | Finegold |
| 2005/0053660 A1 | 3/2005 | Beckert et al. |
| 2005/0175565 A1 | 8/2005 | Duranton et al. |
| 2006/0198886 A1 | 9/2006 | Jenkins |
| 2010/0166872 A1 * | 7/2010 | Singh et al. ................... 424/499 |

FOREIGN PATENT DOCUMENTS

| EP | 1116488 A2 | 7/2001 |
| WO | 99/34805 A1 | 7/1999 |
| WO | 01/39763 A2 | 6/2001 |

OTHER PUBLICATIONS

A. R. Kennedy et al.: "Two new compounds by reaction of taurolidine with methylene glycol," Acta Cryst., C55, pp. 232-234, 1999.

\* cited by examiner

*Primary Examiner* — Brian Gulledge
(74) *Attorney, Agent, or Firm* — Rothwell, Figg, Ernst & Manbeck, P.C.

(57) ABSTRACT

It now has been found that oral administration of pharmaceutical agents, including N-methylol transfer agents such as Taurolidine may be used to provide efficacious blood plasma concentration of the agents for treatment of diseases by providing release of the active agent into the duodenum or jejunum of a patient and/or at a pH of about 5.4 to about 6.5. Embodiments of the invention therefore provide oral dosage forms, compositions and methods for administration of pharmaceutical agents to the duodenum or jejunum of a patient, and/or which release at a pH of about 5.4 to about 6.5.

16 Claims, 7 Drawing Sheets

Fig. 1

Taurolidine

Taurultam

Fig. 2

R = alkyl, aryl, hydrogen, or hetero group or atom

Fig. 3

R = alkyl, aryl, hydrogen, or hetero group or atom

Fig. 4

R = alkyl, aryl, hydrogen, or hetero group or atom

Fig. 5

R = alkyl, aryl, hydrogen, heteroatom or heterogroup

METHODS AND COMPOSITIONS FOR ORAL PHARMACEUTICAL THERAPY

CROSS REFERENCE TO RELATED APPLICATIONS

This application is a 35 U.S.C. §371 National Phase Entry Application from PCT/IB2011/001539, filed Jun. 1, 2011, and designating the United States, which claims benefit of U.S. provisional application no. 61/350,183 filed on Jun. 1, 2010, and U.S. provisional application no. 61/370,315 filed Aug. 3, 2010, all of which is incorporated herein by reference in its entirety for all purposes.

BACKGROUND OF THE INVENTION

1. Technical Field

The invention relates to the field of oral medicament administration. In particular, embodiments of the invention concern oral formulations of pharmaceutically useful compositions, for example, N-methylol transfer agents (methylol donating compounds) such as Taurolidine and Taurultam.

2. Description of the Background Art

Taurolidine, Taurultam, N-methylol taurinamide and the like are antineoplastic and antimicrobial compounds that do not exhibit the phenomenon of resistance due to their mechanism of action, which involves a cross-linking reaction with the cell wall of bacteria and with tumor cells. It is known that solutions containing Taurolidine or Taurultam can be used successfully intra-operatively and post-operatively in oncological surgery for intravenous delivery or instillation into a body cavity, for example. In these known methods, as for many pharmaceutical treatment methods, it is important to bring sufficiently high concentrations of the drug (for example, Taurolidine, Taurultam, N-methylol-taurultam and the like) into direct contact with the cells to be treated, such as tumor cells or bacteria, over a long enough time period. For Taurolidine when used for bacterial infection or oncological treatment, concentrations at or near bacteria or the tumor cells preferably should be within a range of from about 2 µg/mL to about 80 µg/mL. In general, higher amounts within this range are required to kill tumor cells by apoptosis without necrosis. Lower levels of the N-methylol transfer agents within this range generally are sufficient to inhibit angiogenesis and tubulogenesis by inhibition of vascular endothelial growth factor (VEGF). This constrains up-growth of new blood vessels and uncontrolled growth of the tumor. Because of the need for relatively high concentrations of N-methylol transfer agent in the blood, serum or plasma and the very poor aqueous solubility of Taurolidine and Taurultam, isotonic solutions of Taurolidine (0.5% to 2.0%) in Ringer's solution usually are administered locally by instillation during surgery in large volumes.

Large amounts of solution also are administered intravenously via a central line or port drips in daily dosages of 4 times 250 mL 2% solution. In routine clinical use for cancer or for infection by bacteria or other infectious agents, these administrations should be delivered for several continuous days, however for practical reasons it is difficult to administer intravenous infusions of this type in the hospital for more than 14 days. Difficulties also may arise due to the large volumes of Taurolidine solution required for infusion, lack of electrolytes, etc. Administration at home is possible, but only in limited circumstances or exceptional cases because of the complex treatment procedure and the high risk of catheter sepsis. Therefore, the use of N-methylol transfer agents in cancer treatment or for treatment of microbial infections, while useful, has certain drawbacks.

There continues to be a need for new formulations that allow oral treatment of neoplastic, infectious and other diseases in which oral dosing can provide adequate blood concentrations of the compound for effective treatment, without the need for long-term intravenous infusion, with its dangers and inconveniences, or other more invasive administration methods.

SUMMARY OF THE INVENTION

Accordingly, embodiments of the invention provide an oral composition for introducing an N-methylol transfer agent into a subject's bloodstream where oral administration of this composition provides an efficacious blood, serum or plasma level of the N-methylol transfer agent in the body of a subject to treat disease. For example, the composition can comprise the agent in combination with a pharmaceutically acceptable delayed release carrier, wherein, upon oral administration, the carrier (a) carries the agent through said subject's stomach and releases the agent into said subject's duodenum or jejunum (e.g., upper jejunum) so as to permit the agent to enter the subject's bloodstream through the duodenum or jejunum, (b) releases the agent at a pH of about 5.4 to about 6.5, or (c) both. In addition, further embodiments comprise at least one N-methylol transfer agent or derivative thereof, such as Taurolidine, Taurultam, 1183B (cyclo-taurolidine), N-methylol taurinamide and any combination thereof. According to certain embodiments, the agent comprises Taurolidine, Taurultam or a combination thereof. Certain oral compositions employ a carrier which releases the agent into the duodenum or the jejunum of the subject according to certain embodiments.

The oral compositions according to the invention can be formulated as a tablet or as a capsule, and may use a targeted release carrier which may comprise an enteric coating that delays release of the active agent until after passage through the stomach. Such enteric coatings can comprise a co-polymer of methacrylic acid and methyl acetate or methacrylic acid and ethyl acrylate.

Certain embodiments of the invention are suitable to and can introduce a concentration of the agent into the bloodstream of the subject of at least about 2 µg/mL, at least about 4 µg/mL, at least about 5 µg/mL, at least about 10 µg/mL, at least about 20 µg/mL, up to about 80 µg/mL. Certain embodiments can introduce a concentration of the agent into the bloodstream of the subject within a range of about 2 µg/mL to about 80 µg/mL, about 2 µg/mL to about 40 µg/mL, about 2 µg/mL to about 30 µg/mL, about 2 µg/mL to about 20 µg/mL, about 4 µg/mL to about 80 µg/mL, about 4 µg/mL to about 40 µg/mL, about 4 µg/mL to about 30 µg/mL, about 4 µg/mL to about 20 µg/mL, about 5 µg/mL to about 80 µg/mL, about 5 µg/mL to about 40 µg/mL, about 5 µg/mL to about 30 µg/mL, about 5 µg/mL to about 20 µg/mL, about 10 µg/mL to about 80 µg/mL, about 10 µg/mL to about 40 µg/mL, about 10 µg/mL to about 30 µg/mL, about 10 µg/mL to about 20 µg/mL, about 20 µg/mL to about 80 µg/mL, about 20 µg/mL to about 40 µg/mL, or about 20 µg/mL to about 30 µg/mL.

Embodiments of the invention also provide uses of the N-methylol transfer agents in the manufacture of an oral medicament to produce an efficacious serum or plasma level of the agent in the body. Also included are methods of treating a disease or introducing a pharmaceutical agent into the bloodstream of a subject, comprising oral administration of one or more of the oral compositions described above to the subject. The disease can be a neoplastic disease. In certain methods, the agent is an N-methylol transfer agent, such as Taurolidine, Taurultam, 1183B (cyclo-taurolidine), N-methylol taurinamide, a substance which forms N-methylol taurinamide, or any combination thereof. According to certain embodiments, the agent is Taurolidine, Taurultam, or a combination thereof.

Embodiments of the invention provide use of an agent in the manufacture of a medicament for treating a disease, e.g., a neoplastic or infectious disease, wherein the medicament is formulated to provide release of the agent in the duodenum or jejunum of a patient or to release the agent at a pH of about 5.4 to about 6.5, e.g., about pH 5.5 or higher. In certain uses, the agent is an N-methylol transfer agent such as Taurolidine, Taurultam, 1183B (cyclo-Taurolidine), N-methylol taurinamide, or any combination thereof.

Further embodiments of the invention also provide a method of introducing an agent into a subject's bloodstream, comprising orally administering the agent to the subject in combination with a pharmaceutically acceptable targeted release carrier, wherein, upon oral administration, the carrier (a) carries the agent through the subject's stomach and releases the agent into the subject's duodenum or jejunum so as to permit the agent to enter the subject's bloodstream through the duodenum or jejunum, (b) releases the agent at a pH of about 5.4 to about 6.5, or (c) both.

Certain methods of this type employ a targeted release carrier which comprises an enteric coating. Certain methods use a targeted release carrier that releases said agent into said subject's duodenum or jejunum (e.g., upper jejunum). Certain methods also employ an agent which is a N-methylol transfer agent, such as Taurolidine, Taurultam, 1183B (cyclo-taurolidine), N-methylol taurinamide or any combination thereof.

In certain methods, the composition introduces a concentration of the agent into the bloodstream of the subject of at least about 2 µg/mL, at least about 4 µg/mL, at least about 5 µg/mL, at least about 10 µg/mL, at least about 20 µg/mL, up to about 80 µg/mL. The composition may introduce a concentration of the agent into the bloodstream of said subject within a range of about 2 µg/mL to about 80 µg/mL, about 2 µg/mL to about 40 µg/mL, about 2 µg/mL to about 30 µg/mL, about 2 µg/mL to about 20 µg/mL, about 4 µg/mL to about 80 µg/mL, about 4 µg/mL to about 40 µg/mL, about 4 µg/mL to about 30 µg/mL, about 4 µg/mL to about 20 µg/mL, about 5 µg/mL to about 80 µg/mL, about 5 µg/mL to about 40 µg/mL, about 5 µg/mL to about 30 µg/mL, about 5 µg/mL to about 20 µg/mL, about 10 µg/mL to about 80 µg/mL, about 10 µg/mL to about 40 µg/mL, about 10 µg/mL to about 30 µg/mL, about 10 µg/mL to about 20 µg/mL, about 20 µg/mL to about 80 µg/mL, about 20 µg/mL to about 40 µg/mL, or about 20 µg/mL to about 30 µg/mL.

Certain embodiments also provide oral compositions and uses thereof wherein the composition contains a corticosteroid. Exemplary compositions include combinations of an agent, e.g. an N-methylol transfer agent such as Taurolidine and/or Taurultam, and a corticosteroid. Methods for introducing an agent into the bloodstream of a subject or of treating a disease comprising administering these compositions also are provided.

DETAILED DESCRIPTION OF THE PREFERRED EMBODIMENTS

The concentration of a pharmaceutical agent in the bloodstream is important to provide efficacy of the agent in the treatment of the disease(s) it is designed to combat in the body. Some agents, however, are not administered orally because the agent is susceptible to degradation or other deleterious effects when taken orally and exposed to gastric fluids or other reasons. For example, some compounds must achieve a minimal level in the serum or plasma in order to be effective, and this level is difficult to achieve using an oral medication. Generally, such compounds must be administered by a different route to obtain a sufficiently high blood concentration of the agent in the patient. These alternate routes of administration, such as intravenous injection or infusion, or other forms of injection, are not as convenient, particularly for use in the home, as the oral route, and are not preferred by patients. The compositions and methods of this invention allow certain pharmaceutical agents to be administered orally and still achieve suitably high blood or plasma concentrations for effectiveness.

Taurolidine and other N-methylol transfer agents have been found to be effective in killing, reducing, inhibiting, or retarding growth of microbial cells, including bacteria and fungi, as well as tumor cells, including tumor cells which are refractory to cytotoxicity by other known chemotherapeutic agents, but to be well-tolerated by normal cells and even stem cells. N-Methylol-containing or N-methylol-donating compounds such as Taurolidine exert their cytotoxic activity by a mechanism different from standard chemotherapeutic agents or antibiotics. These N-methylol transfer agents are able to induce apoptosis in tumor cells or kill microbial cells by irreversibly transferring a methylol group to the cell surface. The compound itself or a methylol molecule produced by the compound binds to a component, such as a cell surface polypeptide ligand or other cell surface moiety, to initiate an intracellular signal transduction cascade culminating with cell death, e.g., by apoptosis. Taurolidine acts by transferring three methylol groups at the site of action. Taurultam is an intermediate metabolite of Taurolidine, which transfers a single methylol group with liberation of the very well tolerated compound taurinamide, and biotransformation to taurin and carbon dioxide. Thus, methylol transfer is distinct from the mechanism of methyl transfer, which is characteristic of many highly toxic anti-tumor drugs. Taurolidine and Taurultam have low toxicity and are not cytotoxic against normal cells.

The terms "N-methylol transfer agent" and "N-methylol donating compound" and cognates thereof indicate a compound which contains or is capable of producing a methylol molecule under physiological conditions. N-methylol transfer agents include compounds such as Taurolidine and Taurultam, and their derivatives, including taurinamide and urea derivatives. The compounds Taurolidine and Taurultam are disclosed in U.S. Pat. No. 5,210,083, which is incorporated herein by reference.

Certain N-methylol transfer agents are Taurolidine, Taurultam, and mixtures thereof. Other suitable N-methylol-containing compounds include taurinamide derivatives and urea derivatives, examples of which are identified herein and shown in the Figures. Examples of specific derivatives of Taurolidine, Taurultam, taurinamide and urea which may be useful in the present invention also can be found in WO 01/39763A2, the disclosures of which are hereby incorporated by reference.

A "derivative" of Taurolidine or Taurultam refers to a sulfonamide compound which possesses at least 10% of the neoplastic activity of Taurolidine or Taurultam, respectively. Some examples of such compounds include but are not limited to 1,3,-dimethylol-5,5-dimethylhydantoin, hexamethylene tetramine, or noxythiolin. See FIGS. 2-5 for structures of exemplary compounds. N-methylol transfer agents which are suitable for use with the invention include Taurolidine and the related compound Taurultam, although any active N-methylol transfer agent may be used according to the invention. Other N-methylol transfer agents contemplated for use with the invention include cyclotaurolidine or N-methyltaurinamide.

N-methylol transfer agents are an example of pharmaceutical agents that previously have not generally or successfully been administered orally to achieve an efficacious blood, plasma or serum concentration. In particular, N-methylol transfer agents typically have been administered by injection or instillation, either intravenously, into a body cavity, or by direct injection into the tumor or near the tumor site. It is desirable for patients to avoid the discomfort and inconvenience of such more invasive administration methods, which until now have been necessary for patients to reap the benefit of N-methylol transfer agent therapies. Therefore, the invention is contemplated to be useful for administration of antineoplastic and/or microbial compositions, including N-methylol transfer agents. However any suitable pharmaceutical agent may advantageously be used with the compositions and methods of the invention described herein. Further compositions may provide a combination of a corticosteroid and/or an antineoplastic agent with an N-methylol transfer agent.

Surprisingly, it now has been found that Taurolidine, Taurultam and other N-methylol transfer agents, for example, may be used successfully to treat disease, for example infectious disease and neoplastic disease, with oral administration. In particular, targeted release oral dosage forms such as capsules or microcapsules according to the invention can be used to achieve concentrations of the drug in patient blood, plasma or serum of, for example, 20 µg/mL. This concentration is in the range suitable for apoptotic killing of tumor cells and is at or above the range needed to treat microbial, e.g., bacterial infection, or inhibit angiogenesis and tubulogenesis. This provides the opportunity for patients to receive anti-neoplastic treatment or treatment for microbial disease, e.g., a bacterial or fungal infection, at home with oral medication. This oral treatment may be administered in conjunction with or after intravenous infusion and/or intraperitoneal instillation during surgery for tumor or abscess or as palliative treatment for tumor patients for whom surgery is not an option and/or in which the conventional anti-neoplastic chemotherapeutic drugs are no longer effective, to at least stop aggressive tumor growth and metastasis formation and to stabilize tumor disease.

As used herein, the terms "treat" or "treatment" include reducing, inhibiting, retarding, or stopping growth of neoplastic and/or microbial cells. The terms "treat" or "treatment" include killing such cells, as well as reducing, inhibiting, retarding or stopping growth of tumors, including malignant tumors, or reducing size of such tumors.

Accordingly, embodiments of the invention provide formulations of pharmaceutical agents for oral administration. Certain embodiments involve Taurolidine and/or Taurultam for oral administration that have a retarded or delayed release of the compounds such that they are released into the upper intestinal tract, such as in the duodenum, in transit to the jejunum, or in the jejunum (e.g., the upper jejunum) at a pH level of approximately 5.4-6.5, e.g., 5.5-6.0. The formulations of the invention may be used with Taurolidine, Taurultam, compound 1183B (also sometimes referred to as cyclotaurolidine), N-methylol taurinamide or any N-methylol-donating compound or mixture thereof, or any suitable agent. Cyclo-taurolidine is not stable in aqueous medium and is transformed into Taurolidine and methylene glycol, however the invention described herein allows this compound to be administered orally and still achieve serum concentration levels suitable for therapy, e.g. of cancer.

The invention includes embodiments which may further incorporate administration of another medication such as a corticosteroid. The other medication can be administered before, during or after administration of the inventive composition. Exemplary corticosteroids which can be used in the invention include hydrocortisone (cortisol), cortisone, prednisone, prednisolone, methylprednisolone, triamcinolone, mometasone, flucinolone, betamethasone, dexamethasone, fluocortolone, clobetasone, prednicarbate, halcinonide, budesonide, desonide, and fluprednidene.

The oral dosage formulation may have a targeted release carrier, such as an enteric coating, which operates in a manner to avoid release of the drug into the stomach, which could produce an adverse event such as acid regurgitation, local irritation of the stomach or an undesirable reaction of the medicament with the low pH environment of the stomach. At the pH range of 1-4, which is present in the stomach, Taurolidine and other drugs can be at least partially hydrolyzed, resulting in a loss of bioavailability. The pH of the duodenum generally is about 5.5, a much less harsh environment. Therefore, the formulation should primarily or substantially release an efficacious amount of the agent only after passage through the stomach, e.g., in the upper intestinal tract, e.g., the duodenum or jejunum (e.g., upper jejunum), to allow maximum absorption of the drug. If the drug is released in the colon or lower small intestine, it is possible that the agent could be eliminated, reduced, or degraded by reacting with intestinal flora before absorption, also potentially resulting in loss of systemic bioavailability and lower blood, plasma or serum concentrations of the drug.

The inventive compositions and methods therefore relate to targeted release formulations of agents and methods of administration that can result in a high level of the active compound in patient blood, plasma or serum when the compound is administered orally. The compositions may release the active compound at or near a pH of about pH 5.4-6.5, e.g., about pH 5.5-6.0, in the upper intestinal tract after the stomach, such as in the duodenum or the jejunum (e.g., the upper jejunum). This location for drug release maximizes the bioavailablility of orally administered agents and avoids degradation of the compound by both acid in the stomach and the potential for exposure to premature elimination or action by intestinal flora. The invention thus is targeting to release the active agent in an area of the intestine having low bacterial population.

Any oral dosage form is suitable for use with the invention, including coated tablets, caplets, and hard or soft capsules, which have been formulated for or treated so as to release the agent in the desired locations described herein. Tablets may be formed by pressing, and then coating. In order to produce a suitable targeted release form, one method is to use a coating to produce a dosage form resistant to gastric juices, such as a tablet, capsule or other oral dosage form. Examples of known coatings include co-polymers based on methacrylic acid/ethyl acrylate or methacrylic acid/methyl acrylate such as Kollicoat™ or Eudragit™. Certain dosage forms are hard gelatin capsules, size 0 (zero), single opac with a filling volume of 270 mg, or size 0 capsules with an elongated base part, for which the filling volume may be increased by 10%, which are coated with a suitable enteric coating. However, any pharmaceutical formulation which releases at least a majority of the active compound into the duodenum or jejunum may be used. Larger crystals can allow higher dosages for the same volume, as can compression of the crystals, in which 300-400 mg dosages can be achieved, or even higher.

Any suitable conventional or convenient tablet or capsule form may be used. For example, capsules of hard gelatine or hydroxypropylmethyl cellulose (HPMC) may be suitable; certain dosage forms conveniently are a size 0, elongated capsule. Hard gelatine capsules advantageously may be coated with Eudragit™ L acrylic polymer for delivery of the contents at about pH 5.5 or into the duodenum. HPMC capsules are resistant to gastric juice for time periods up to about 30 minutes and open in the duodenum or at pH values of about 5.5. HPMC capsules may be coated as well, to enhance the stability of the product in gastric juices. A suitable coating for HPMC capsules can include cross-linked polymethacrylate or polyvinylacetate phthalate.

In certain embodiments, to attain a pH-dependent drug release from a capsule or tablet, Eudragit™ L powder is dissolved in an organic solvent such as 10-15% acetone or isopropanol and coated onto the dosage forms by the dipping method. Filled capsules or tablets are dipped for a short time and subsequently dried with, e.g., a blow-dryer or in a vacuum-drying cupboard to remove the organic solvent. Any suitable coating method is contemplated for use with this method, however. It is also feasible to use a spray-coat method using Eudragit™ L 30 D-55 as an aqueous dispersion using known procedures, for example.

It is expected that the formulations and methods of the invention will be useful in treating any disease where it is desirable to provide an orally administrable dosage form to provide suitable blood concentrations of an active pharmaceutical agent. However, great benefits can be achieved with the invention in the treatment of infectious or neoplastic disease for which injectable agents, such as N-methylol transfer agents, traditionally have been given, including infection by fungi or bacteria, or cancerous disease such as carcinoma, sarcoma or lymphoma.

Infectious disease, such as infection by any fungi or bacteria, is comtemplated for treatment using the invention. The treatment of severe microbial infection, bacteremia and sepsis, accompanied by the presence of massive Gram-negative and Gram-positive bacteria or fungi (i.e. *Candida* spp.) with or without the presence of pus, is quite complex and difficult to treat by conventional methods. Such infections may be treated using the methods and compositions described here. Exemplary infections include, but are not restricted to, nosocomial infections, surgical infections, severe abdominal infections such as peritonitis, pancreatitis, gall bladder empyema, and pleura empyema, bone infections such as osteomyelitis, or any infection. Treatment of septicemia, sepsis and septic shock, infections due to or following use of immunosuppressant drugs, cancer chemotherapy, radiation, contaminated i.v. fluids, haemorrhagic shock, ischaemia, trauma, cancer, immuno-deficiency, virus infections, diabetes, the need for indwelling catheters, breathing apparatus, kidney dialysis port or any implant, tube or catheter are particularly contemplated. Infection or sepsis following exposure to Gram-negative and Gram-positive bacterial organisms may be treated using the inventive compositions and methods or uses.

Specific examples of microbial infection, such as bacterial and/or fungal infection, especially nosocomial infections, which are contemplated for use with the invention include, but are not limited to, infections due to *E. coli*, *Klebsiella* sp., *Enterobacter* sp., *Proteus* sp., *Serratia marcescens*, *Pseudomonas aeruginosa*, *Staphylococcus* spp., including *S. aureus* and coag.-negative *Staphylococcus*, *Enterococcus* sp., *Streptococcus pneumoniae*, *Haemophilus influenzae*, *Bacteroides* spp., *Acinetobacter* spp., *Helicobacter* spp., *Candida* sp., etc. Resistant microbes are included, for example methicillin-resistant *Staphylococcus aureus* (MRSA) and vancomycin-resistant *Enterococcus faecalis* (VRE).

In particular, an example of bacterial diseases which is contemplated for use with this invention are those due to *Stenotrophomonas maltophilia*. *S. maltophilia* is an aerobic, nonfermentative, Gram-negative bacterium which produces an infection in humans which is difficult to treat. Infection may occur more frequently in patients with compromised immune systems and in patients needing a breathing tube, central intravenous line or shunt, or any indwelling catheter, shunt or tube. Common infections with this bacterium can occur in pneumonia, urinary tract infection or blood sepsis.

Cancers such as colon cancer, rectal cancer and colo-rectal cancer, ovarian cancer, breast cancer, prostate cancer, lung cancer, mesothelioma, melanoma, renal cancer, liver cancer, pancreatic cancer, gastric cancer, esophageal cancer, urinary bladder cancer, cervical cancer, cardiac cancer, gall bladder cancer, skin cancer, bone cancer, cancers of the head and neck, central nervous system cancers such as glioma, glioblastoma, neuroblastoma, astrocytoma, and carcinomatous meningitis, leukemia, lymphoma, lymphosarcoma, adenocarcinoma, fibrosarcoma, and metastases thereof, for example, are diseases contemplated for treatment according to embodiments of the invention. Drug resistant tumors, for example a multiple drug resistant (MDR) tumor, also are contemplated for use in treatment methods using the inventive compositions, including drug resistant tumors which are solid tumors, non-solid tumors and lymphomas. It is presently believed that any neoplastic cell can be treated using the methods described herein.

The compositions and methods of the invention also may be used in combination therapy in which the agent, for example an N-methylol-containing compound, is administered before, after, or together with another chemotherapeutic agent or with radiation, surgery or some other treatment modality. Thus, the formulations of the invention also may be administered in combination with (sequentially, simultaneously or separately from) any conventional treatment, such as chemotherapy or radiation, as well as surgery, particularly in treatment of cancer and any neoplastic disease, where combination therapies are quite common. Drugs which may be used in combination with the invention include antineoplastic chemotherapy agents. Also, corticosteroids may be administered in combination with N-methylol transfer agents for treatment of disease. Compounds for co-administration may be formulated in a single dosage form with the N-methylol transfer agent or in a separate dosage form to be administered separately, either at the same time as or at a different time.

When used in the treatment of neoplastic disease with N-methylol transfer agents, the co-administered agent or therapy may treat and/or kill tumors or tumor cells by a different mechanism than N-methylol transfer agents. For example, an antimetabolite, a purine or pyrimidine analogue, an alkylating agent, 5-FU, a crosslinking agent (e.g., a platinum compound), an intercalating agent, a tumor-specific monoclonal antibody (for example, bevacizumab (Avastin™), temozolamid (Temodal™), gemcitabin (Gemzar™), and the like), an anti-angiogenic agent and/or an antibiotic may be administered in a combination therapy regimen. The co-administered drug may be given before, after, or simultaneously with the N-methylol transfer agent. The compositions and formulations of the invention may be used in conjunction with anti-neoplastic antibody therapy, particularly when resistance appears or the potential for developing resistance to these treatments is a concern.

Further embodiments of the invention include co-administration of N-methylol transfer agent and corticosteroids, which may include cortisone, prednisolone and the like, to assist in reducing the volume of swelling. The co-administration may occur before, after, or in conjunction with the administration of the N-methylol-transfer agent(s).

The formulations of the invention have been used successfully in the treatment of lymphosarcoma (lymphoma) in an extremely ill dog, showing that the oral medication is able to produce plasma or serum levels of a N-methylol transfer agent that are efficacious to treat disease. See Example 10. The dog was treated over three months with two Taurolidine targeted-release capsules daily without obvious adverse events. The conventional prior art treatment for lymphosarcoma in the dog involves three anti-neoplastic chemotherapeutics plus prednisolone, administered intravenously over a six-month period according to a complex schedule. The abbreviated protocol is described in Diavet: aus dem Labor für die Praxis, issue 9/2004, which is incorporated herein by reference, for comparison. Such intravenous treatment in the dog over a long period is nearly impossible to achieve for most patients, and is burdensome. The invention therefore presents an improvement over the products and methods available in the prior art by allowing orally administered therapy which was previously unavailable.

EXAMPLES

Example 1

Taurolidine/Taurultam Gelatin Capsules

Capsules containing the formulation shown in Table I or Table II are manufactured as follows. Normal crystalline or microcrystalline forms of the Taurolidine and/or Taurultam compounds may be used with either formulation.

TABLE I

| Taurolidine/Taurultam Formulation. | | |
|---|---|---|
| No. | Compound | Theoretical Weight (mg/capsule) |
| 1 | Taurolidine | 158.8 |
| 2 | Taurultam | 105.8 |
| 3 | Talc, powder | 4.32 |

TABLE I-continued

| Taurolidine/Taurultam Formulation. | | |
|---|---|---|
| No. | Compound | Theoretical Weight (mg/capsule) |
| 4 | Magnesium stearate | 0.54 |
| 5 | Aerosil-200 | 0.54 |
|   | Capsule | 270 |

TABLE II

| Taurolidine/Taurultam Formulation. | | |
|---|---|---|
| No. | Compound | Theoretical Weight (mg/capsule) |
| 1 | Taurultam | 264.6 |
| 2 | Talc, powder | 4.32 |
| 3 | Magnesium stearate | 0.54 |
| 4 | Aerosil-200 | 0.54 |
|   | Capsule | 270 |

The talc, magnesium stearate and Aerosil-200 are mixed for ten minutes on a gymwheel and strained through a 0.1 mm sieve, then mixed again for ten additional minutes. The Taurultam or Taurolidine/Taurultam then are added and mixed for another ten minutes on the gymwheel. This mixture is strained through a sieve with a 0.5 mm mesh size and the mixture is again mixed for ten minutes. The formulation is filled into size 0 capsules using an Appro Pharm™ capsule device, with pounding 10 times, re-filling, closure and sealing.

Example 2

Production of Record Hospital Samples, Taurolidine Capsules, 270 mg

Capsule formulations were manufactured using the methods described in Example 1, using the formulation shown in Table III, below.

TABLE III

| Taurolidine Formulation. | | | |
|---|---|---|---|
| No. | Compound | Theoretical Weight (mg/capsule) | Actual Weight (g/preparation for 240 capsules) |
| 1 | Taurolidine | 264.6 | 63.504 |
| 2 | Talc, powder | 4.32 | 1.0368 |
| 3 | Magnesium stearate | 0.54 | 0.12196 |
| 4 | Aerosil-200 | 0.54 | 0.1296 |
|   | Capsule weight | 270 | 64.8 |

Example 3

Production of Methylol Transfer Agent, Compound 11838B.

Three hundred grams Taurolidine (Geistlich™), 3000 mL methylene glycol (36% pure) and 500 mL distilled water were stirred together at room temperature until an almost clear solution was generated. The solution was filtered and the clear filtrate was allowed to stand overnight or at least 14 hours at 5° C.-8° C. in a refrigerator. Product 1183B (cyclo-taurolidine) crystallized. This solid was removed by suction with a syphon and recrystallized from alcohol. Recovery, 220 g, melting point 149° C.-150° C. Infrared spectrum analysis confirmed that this product (1183B) was identical to that reported in Kennedy et al., Acta Cryst. C55:232-234, 1999 (7-oxa-2[$\lambda$]$^6$-thia-1,5-diazabicyclo[3.3.1]nonane-2,2-dione).

Example 4

Manufacture of Gelatin Capsules, Compound 1183B

Gelatin capsules are manufactured according to the methods described in Example 1, using the formulation shown in Table IV, below. Additional capsules are produced with the same capsule containing 450 mg 1183B. This is possible due to a different crystal size of the compound, which allows different filling weight quantities for the same capsule size.

TABLE IV

1183B Formulation.

| No. | Compound | Theoretical Weight (mg/capsule) |
|---|---|---|
| 1 | 1183B | 264.6 |
| 2 | Talc, powder | 4.32 |
| 3 | Magnesium stearate | 0.54 |
| 4 | Aerosil-200 | 0.54 |
|   | Capsule weight | 270 |

Example 5

Determination of Fill Weight for Size 0 Elongated Capsules

HPMC capsules (Capsugel™) were filled with Taurolidine, micronized Taurolidine or Taurultam in a carrier termed FST-Complex according to the following formulations. See Table V. FST-Complex contained 8 parts talc (talc Eu.Ph.), 1 part magnesium stearate (Eu.Ph.) and 1 part Aerosil200™ (Eu.Ph.). Ten gram mixtures were manufactured for each test number, filled into the capsules, and the net weight determined. The effective amount of Taurolidine contained per capsule was calculated from this information. Test 2c (micronized Taurolidine and 2 parts FST-Complex) provided the highest amount of Taurolidine (377.3 mg) in a Taurolidine only formulation. For Taurolidine plus Taurultam formulations, Test 5a (75 parts Taurolidine, 25 parts Taurultam and 2 parts FST-Complex provided the highest amount of Taurolidine (394.5 mg). Using micronized Taurolidine in this formulation yielded a slightly smaller amount of 381.8 mg.

TABLE V

Fill Weight Results and Calculations

| Test Number | Parts Active Ingredient | | | Parts Carrier | Net Filling Weight (mg) | Net Weight Taurolidine (mg) |
|---|---|---|---|---|---|---|
| | Taurolidine | Taurolidine, micronized | Taurultam | FST-Complex | | |
| 1a | 100 |    |    |    | 295 | 295 |
| 1b | 99 |    |    | 1 | 347 | 343.5 |
| 1c | 98 |    |    | 2 | 365 | 357.7 |
| 1d | 97 |    |    | 3 | 369 | 357.9 |
| 2a |    | 100 |    |    | 310 | 310 |
| 2b |    | 99 |    | 1 | 362 | 358.4 |
| 2c |    | 98 |    | 2 | 385 | 377.3 |
| 2d |    | 97 |    | 3 | 388 | 376.4 |
| 3a | 75 |    | 25 |    | 492 | 369 |
| 3b | 50 |    | 50 |    | 535 | 267.5 |
| 3c | 25 |    | 75 |    | 601 | 150.3 |
| 4a |    | 75 | 25 |    | 478 | 358.5 |
| 4b |    | 50 | 50 |    | 518 | 259 |
| 4c |    | 25 | 75 |    | 585 | 146.3 |
| 5a | 75 |    | 25 | 2 | 526 | 394.5 |
| 5b | 50 |    | 50 | 2 | 558 | 279 |
| 5c | 25 |    | 75 | 2 | 647 | 161.8 |
| 6a |    | 75 | 25 | 2 | 509 | 381.3 |
| 6b |    | 50 | 50 | 2 | 538 | 269 |
| 6c |    | 25 | 75 | 2 | 621 | 155.3 |

Example 6

Dosage Forms Incorporating a Corticosteroid

Capsules or tablets are produced according to any of the examples above, which also include a corticosteroid (e.g. hydrocortisone or prednisolone) in the formulation. Suitable doses for prednisolone are 5-80 mg/day; suitable doses for hydrocortisone are 5-250 mg/day.

Example 7

Delayed Release Dosage Forms by Dip-Coating

To produce a dosage form for drug delivery to the duodenum, Eudragit™ L 100-55 powder is dissolved in a 10-15% solution of acetone or isopropanol. Tablets or filled capsules are coated in this solution by dipping for a short time and drying the dipped tablets or capsules. Blow- or vacuum-drying methods, or any suitable method may be used to remove the organic solvent(s).

Example 8

Delayed Release Dosage Forms by Spray-Coating

Eudragit™ L 30 D-55 aqueous dispersion is spray-coated onto methylol transfer agent tablet or capsule dosage forms using suitable equipment in a coating pan.

Example 9

Coating Immersion Process for Hard Gelatin Capsules

Capsules containing Taurolidine (Taurolin™) or compound 1183B, as indicated in Table VI, below, were coated with using Eudragit™ coatings as indicated, with 1-4 immersion coatings. For capsule A in Table VI, the capsules were immersed for 10 minutes in a bath of Eudragit™ S (dissolved in acetone), and then dried by a hot air gun and again immersed in the Eudragit™ solution for 10 seconds. The capsules were again dried overnight in a drying cabinet at 50° C. and left to harden and dry.

In order to discover the ideal amount of coating, capsules were immersed a different number of separate times in a Eudragit™ solution. For capsule B in Table VI, ten capsules each were coated as described for capsule A with 1, 2, 3 or 4 separate immersions to provide coatings of different amounts. After each drying step, the capsules were placed on parchment paper for final drying overnight. The best results for release of the active ingredient into the duodenum or jejunum were achieved with two coating steps.

Capsules containing 1183B also were coated with Eudragit™ liquid (see C in Table VI, below. These capsules also were placed on parchment paper overnight for final drying.

For capsule under D in Table VI, Eudragit™ L-55 solution was made by dissolving Eudragit™ L 100-55 in isopropyl alcohol under vigorous stirring for 60 minutes to produce a 12.5% solution. The capsules were coated by immersion in this solution one time as described above and dried overnight on parchment paper. The capsules were subjected to a final drying in a vacuum cabinet dryer at 40° C. and 20-25 mbar for 24 hours. The weight of ten capsules without coating was 6426 mg and with coating 6466 mg, corresponding to an average of 4 mg of coating material per capsule. Given the diameter of the uncoated capsules (500 mm), the quantity applied (mg/cm²) is calculated: 4 mg/500 mm²=8 mg/1000 mm²=8 mg/10 cm²=0.8 mg/cm². Therefore, the applied quantity is (500 mm²×0.8 mg/cm²)/642.6 mg=0.62%.

These capsules were assayed for disintegration in 0.1N HCl at 36.2° C.-36.8° C. to determine their persistence against gastric juices. Two untreated capsules containing Taurolidine, 270 mg, were placed in at 1000 mL flask. Warmed 0.1 N HCL at 36.6° C., 500 mL, was added with slow rotation at constant temperature. After 4 minutes, the capsules had dissolved. Two capsules coated with Eudragit™ type S were then subjected to the same conditions for 2½ hours, after which time the capsules were still intact. The solution then was neutralized with NaOH and adjusted to pH 7.5. The capsules released their contents after 2 hours.

One capsule of Taurolidine, 270 mg, enteric coated with Eudragit™ type S with two immersions, was placed in a 1000 mL flask. Five hundred milliliters water, pH 7.4, 36.6° C. was added and left with slow stirring at 36.6° C. After 1.25 hours, the capsule shell showed the effects of attack by the solution; after 2 hours, the capsule opened.

Two capsules containing 1183B, 270 or 450 mg, with no enteric coating, were placed in a 1000 mL flask with 500 mL 0.1 N HCl solution at 36.5° C. and left at this temperature with slow stirring. The capsules dissolved in about 4-7 minutes. The same capsules with a coating of Eudragit type L in isopropyl alcohol, two immersions were subjected to the same treatment at 36.6° C. After one hour, the capsules showed only slight effects of attack by the solution.

TABLE VI

Immersion Coated Capsule Formulations.

| Capsule | Eudragit ™ material | Number of Immersion Coatings |
|---|---|---|
| A. TAUROLIN ™, 270 mg | Eudragit ™ liquid (type S, 12.5% in acetone) | 2 |
| B. TAUROLIN ™, 270 mg | Eudragit ™ L (12.5% in isopropyl alcohol) | 1, 2, 3, 4 |
| C. 1183B, 270 mg-450 mg | Eudragit ™ L (12.5% in isopropyl alcohol) | 1 |
| D. TAUROLIN ™, 270 mg | Eudragit ™ L-55 (12.5% in isopropyl alcohol) | 1 |

The stability of capsules to acidic, neutral or alkaline gastric or intestinal juices is increased with additional immersions in the Eudragit™ solutions in acetone or isopropyl alcohol to allow the capsules to release the active ingredient in the duodenum or jejunum or to allow release lower in the intestine (colon) only. Certain of the capsules were coated using two immersions.

Example 10

Treatment of Lymphosarcoma in Vivo

A six-year-old female Hovawart dog, weight 22 kg, presented with a small, palpable mass in the rectum with perianal bleeding. Histological examination of the tumor revealed, in two samples, that only small residues of intestinal mucosa were present. The remaining areas were ulcerated. The intestinal wall was no longer identifiable because of a massive, diffuse malignant growth of a unique population of rounded cells, mainly stored very densely. The cells had rounded, partially crenated nuclei, often with prominent nucleoli. The cytoplasm was limited indistinctly, presumably narrow. No limitation of the neoplasia was discernable. Hyperplasia of the lymph nodes and lymph node swelling also was noted. The animal had a very bad general state of health, with tachycardia, hyperventilation and black stool. Blood work showed elevations in the number of neutrophils, band granulocytes and lymphocytes, and elevated alkaline phosphatase and lactate dehydrogenase. Thyroid stimulating hormone levels were slightly decreased. Radiography indicated massive mediastinal lymph node involvement and lung metastasis. Occult blood was found in the stool. Lymphosarcoma was diagnosed (mediastinal tumor with space demand), with disadvantageous prognosis.

The dog was treated with transanal polypectomy, punch biopsy before 14 days, and removal of the rectal polyp with stepwise submucosal excision. This was followed by chemotherapy beginning on Day 0 with prednisolone (as a cytotoxic agent for lymphatic cells), maximum dosage of 1 mg/kg for 14 days, followed by a slowing of the dose. Beginning on day 6, Taurolidine capsules produced according to Example 2, with enteric coating, were administered, one capsule two times per day, orally. The oral treatment with Taurolidine continued for three months.

Figure 6:
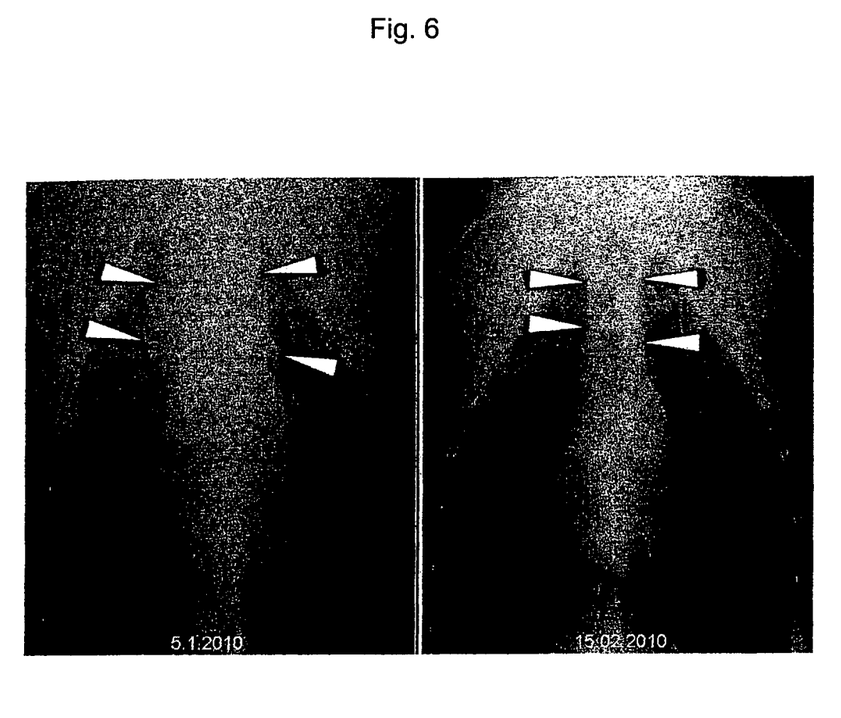
FIG. 6 is an antero-posterior radiograph of the chest of a dog before and after treatment according to an embodiment of the invention.
Figure 7:
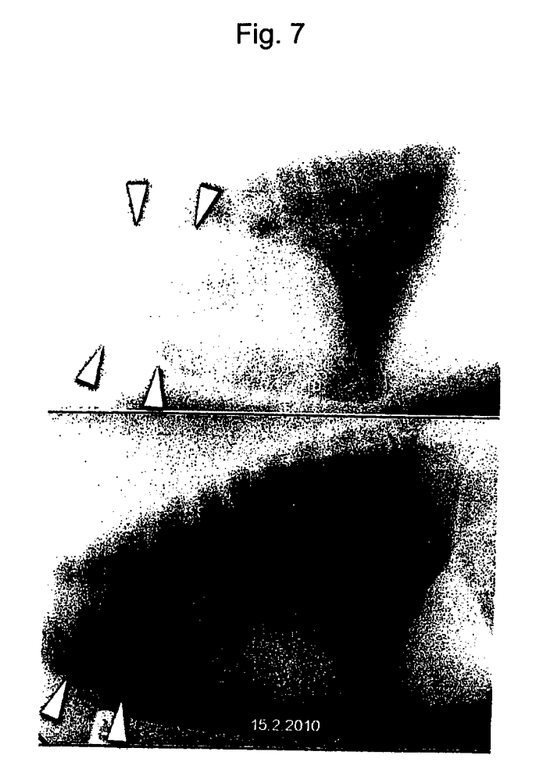
FIG. 7 is a lateral radiograph of the chest of a dog before and after treatment according to an embodiment of the invention.

Forty-one days after treatment began, the animal had a significantly improved general state of health, was stable, had inconspicuous behavior, and had gained 2 kg in weight. Examination revealed the following findings. The number of neutrophils and band granulocytes had dropped significantly and other blood count results were within normal. Lactate dehydrogenase levels were only slightly increased and the stool was negative for occult blood. The radiograph was without findings in the medistinal area and lung. No side effects of the treatment were observed. See FIGS. 6 and 7, which are an antero-posterior radiograph of the chest before (left) and after (right) the treatment (FIG. 6) and a lateral radiograph of the chest before (top) and after (bottom) the treatment (FIG. 7). Before treatment, extensive widening of the mediastinum caused by the large tumor masses is seen in FIG. 6 and complete obliteration of the retrosternal space is seen in FIG. 7. After treatment, the tumor masses were no longer visible.

Example 11

Oral Administration to Achieve Efficacious Blood Levels

Oral dosage forms according to the invention, for example as described in Examples 1-9 above, are administered to subject to achieve levels of N-methylol transfer agents in the blood, serum or plasma within a range of about 2-80 micrograms/mL. Appropriate subjects for treatment include animal and human patients who are suffering from any disease for which an N-methylol transfer agent is indicated, for example a neoplastic disease or an infection by bacteria or fungi.

The invention claimed is:

1. A method of achieving a blood, serum, or plasma level in a subject of at least about 4 µg/mL of an N-methylol transfer agent comprising taurolidine, taurultam, a derivative of taurolidine or taurultam, or a combination thereof, comprising administering to said subject a capsule comprising the N-methylol transfer agent and a pharmaceutically acceptable targeted release carrier, said targeted release carrier providing an efficacious blood, serum or plasma level of said N-methylol transfer agent in said subject, after oral administration of said capsule, to treat a disease in said subject, wherein, after said oral administration, said carrier
   (a) carries said agent substantially intact through said subject's stomach and releases said agent into said subject's duodenum or jejunum, wherein said agent enters the subject's bloodstream through said duodenum or jejunum,
   (b) releases said agent at a pH of about 5.4 to about 6.5, wherein said agent enters the subject's bloodstream, or
   (c) both.

2. The method of claim 1, wherein said disease is a neoplastic disease.

3. The method of claim 2, wherein said neoplastic disease is selected from the group consisting of a carcinoma, a sarcoma and a lymphoma.

4. The method of claim 2, wherein said neoplastic disease is selected from the group consisting of colon cancer, rectal cancer, colo-rectal cancer, ovarian cancer, breast cancer, prostate cancer, lung cancer, mesothelioma, melanoma, renal cancer, liver cancer, pancreatic cancer, gastric cancer, esophageal cancer, urinary bladder cancer, cervical cancer, cardiac cancer, gall bladder cancer, skin cancer, bone cancer, a head cancer, a neck cancer, a central nervous system cancer, glioma, glioblastoma, neuroblastoma, astrocytoma, carcinomatous meningitis, leukemia, lymphoma, lymphosarcoma, adenocarcinoma, fibrosarcoma, and metastases thereof.

5. The method of claim 1, wherein said an infectious disease.

6. The method of claim 5, wherein said infectious disease is due to a bacterial or fungal infection.

7. The method of claim 5, wherein said infectious disease is due to Stenotrophomonas maltophilia.

8. The method of claim 2 further comprising administering a corticosteroid to said subject.

9. The method of claim 1, wherein said agent is released at a pH of 5.5 or higher.

10. The method of claim 1, wherein said N-methylol transfer agent is selected from the group consisting of Taurolidine, Taurultam, 1183B (cyclo-taurolidine), N-methylol taurinamide and any combination thereof.

11. The method of claim 1, wherein said N-methylol transfer agent is Taurolidine, Taurultam, or a mixture thereof.

12. The method of claim 1, wherein said targeted release carrier comprises an enteric coating.

13. The method of claim 12, wherein said enteric coating comprises a co-polymer of methacrylic acid and methyl acetate or methacrylic acid and ethyl acrylate.

14. The method of claim 1, said dosage achieves a blood, serum or plasma level of said N-methylol transfer agent within a range of about 4 µg/mL to 80 µg/mL.

15. The method of claim 1, said dosage achieves a blood, serum or plasma level of said N-methylol transfer agent of at least about 20 µg/mL.

16. The method of claim 1, wherein said dosage achieves a blood, serum or plasma level of said N-methylol transfer agent of at least about 10 µg/mL to 20 µg/mL.

* * * * *

UNITED STATES PATENT AND TRADEMARK OFFICE
CERTIFICATE OF CORRECTION

| | | |
|---|---|---|
| PATENT NO. | : 9,028,866 B2 | Page 1 of 3 |
| APPLICATION NO. | : 13/701372 | |
| DATED | : May 12, 2015 | |
| INVENTOR(S) | : Pfirrmann et al. | |

It is certified that error appears in the above-identified patent and that said Letters Patent is hereby corrected as shown below:

IN THE DRAWINGS

Figure 1:
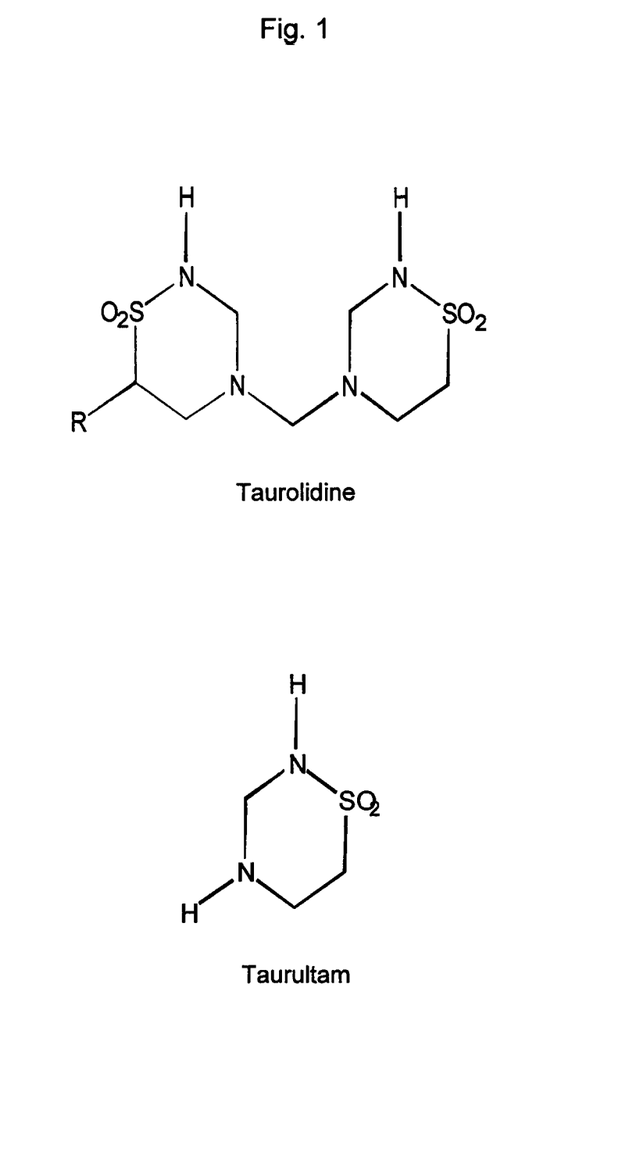
FIG. 1 provides the chemical structures of Taurolidine and Taurultam.
Figure 2:
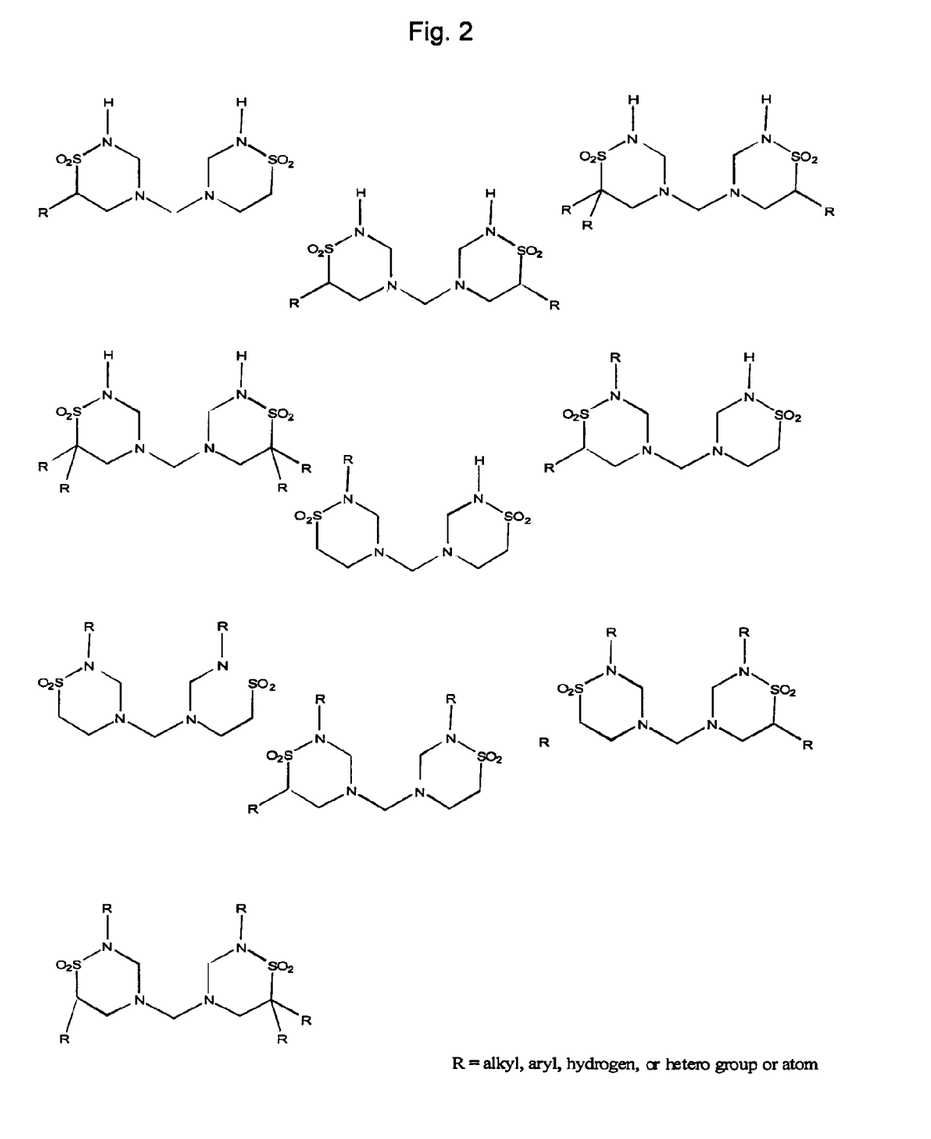
FIG. 2 provides the chemical structures of exemplary Taurolidine derivatives.
Figure 3:
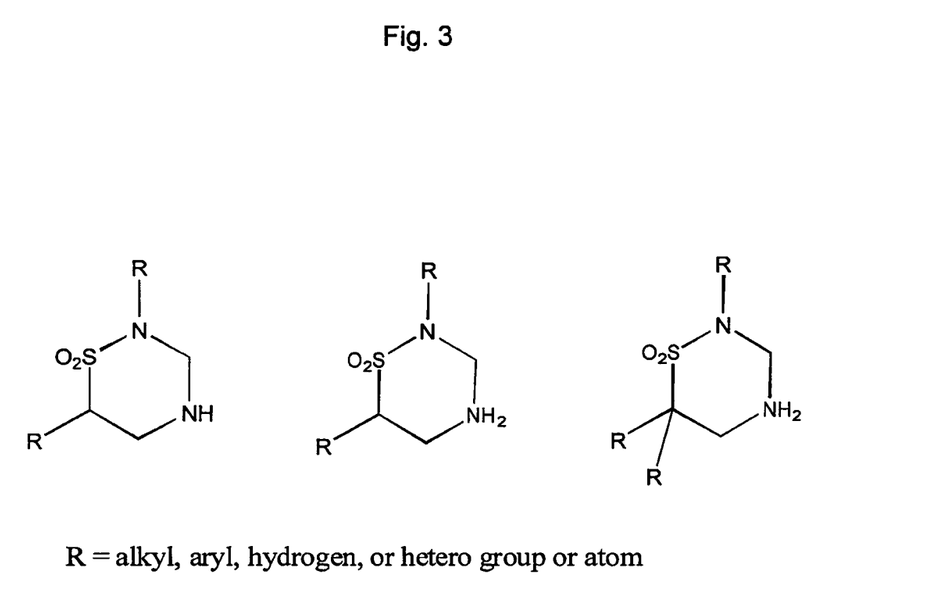
FIG. 3 provides the chemical structures of exemplary Taurultam derivatives.
Figure 4:
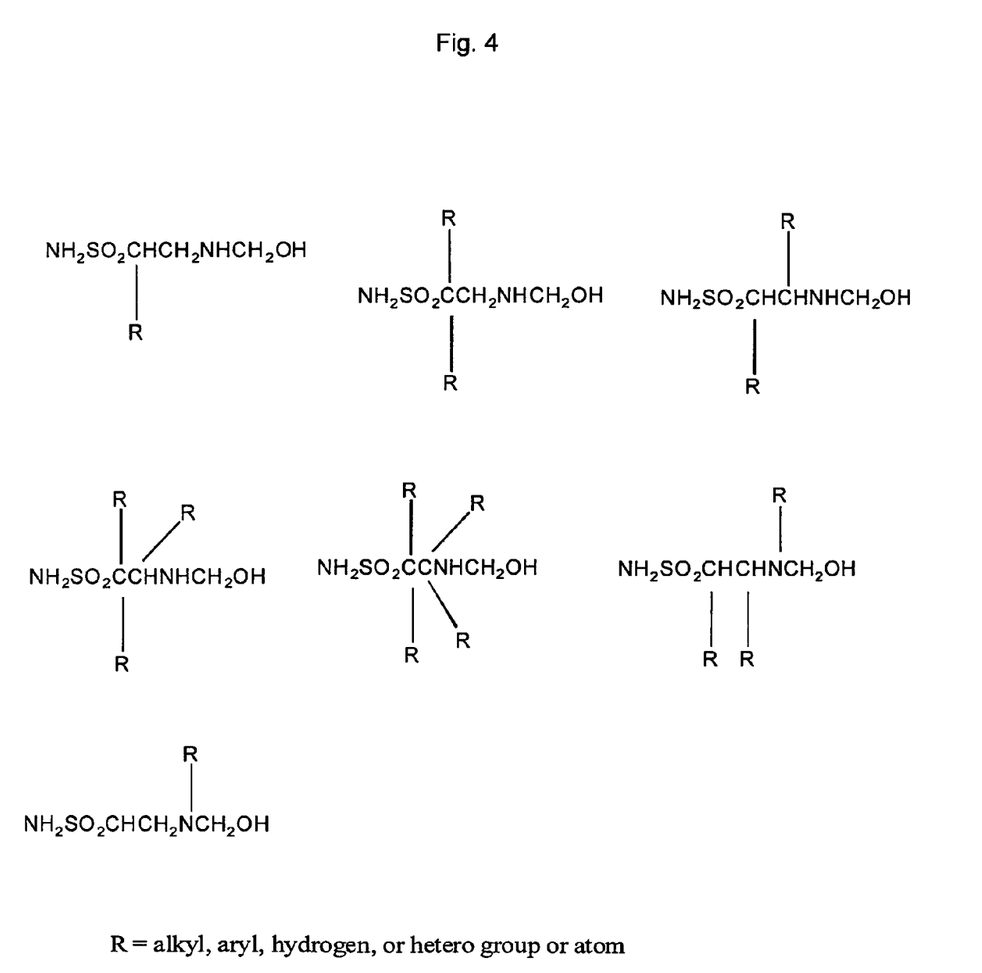
FIG. 4 provides the chemical structures of exemplary taurinamide derivatives.
Figure 5:
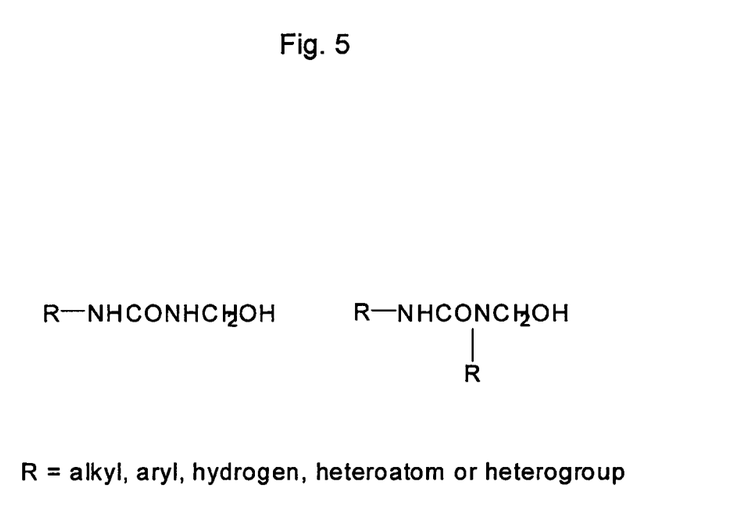
FIG. 5 provides the chemical structures of exemplary urea derivatives.

Figures 3 and 5 should read as shown on the attached drawings sheets.

Signed and Sealed this
Third Day of November, 2015

Michelle K. Lee
*Director of the United States Patent and Trademark Office*

Fig. 3

R = alkyl, aryl, hydrogen, or hetero group or atom

Fig. 5

R—NHCONHCH$_2$OH         R—NHCONCH$_2$OH
                                    |
                                    R

R = alkyl, aryl, hydrogen, heteroatom or heterogroup